United States Patent [19]

Ries et al.

[11] 4,238,963
[45] Dec. 16, 1980

[54] TEST HEAD FOR ULTRASONIC TESTING OF STRUCTURAL MATERIAL

[75] Inventors: Karl Ries, Mülheim; Dieter Lather, Rheurdt; Dieter Kaiser, Mülheim; Kurt Hannoschöck, Sonsbeck; Günter Simoneit, Mülheim, all of Fed. Rep. of Germany

[73] Assignee: Mannesmann Aktiengesellschaft, Dusseldorf, Fed. Rep. of Germany

[21] Appl. No.: 912,712

[22] Filed: Jun. 5, 1978

[30] Foreign Application Priority Data

Jun. 9, 1977 [DE] Fed. Rep. of Germany ....... 2726400

[51] Int. Cl.³ .............................................. G01N 29/00
[52] U.S. Cl. ........................................ 73/644; 73/1 R
[58] Field of Search ............ 73/1 R, 1 DV, 627, 629, 73/632, 644, 290 V; 310/335, 336

[56] References Cited

U.S. PATENT DOCUMENTS

| 2,869,108 | 1/1959 | Smith, Jr. ........................... 73/290 V |
| 3,184,969 | 5/1965 | Bolton ................................ 73/290 V |
| 3,677,061 | 7/1972 | Visser ..................................... 73/1 R |
| 4,090,407 | 5/1978 | Shuler et al. ................... 73/290 V X |
| 4,130,018 | 12/1978 | Adams et al. ..................... 73/290 V |

Primary Examiner—Charles A. Ruehl
Attorney, Agent, or Firm—Smyth, Pavitt, Siegemund, Jones & Martella

[57] ABSTRACT

The test head includes its own calibration device in form of a wire or a bore in front of the transducing surface so that a distinguishable calibration echo is always available.

3 Claims, 2 Drawing Figures

TEST HEAD FOR ULTRASONIC TESTING OF STRUCTURAL MATERIAL

BACKGROUND OF THE INVENTION

The present invention relates to improvements in the nondestructive testing of structural materials, and more particularly, the invention relates to an ultrasonic test head and transducer.

Ultrasonic test equipment for structure parts such as pipes or the like, usually require a particular orientation of such parts relative to the test transducer, particularly if a part moves while it is being examined. Moreover, the equipment requires calibration in order to permit interpretation of any signal being picked up. Particularly, the test equipment includes ultrasonic transducers coupled in a suitable manner to the test object and launch test signals into that object. The latter will return echo signals which have different significance. Legitimate boundaries as well as internal inhomogeneities, flaws, cracks, etc., all may produce echos. The transit time as well as the amplitude of such echos constitute informative parameters which require interpretation. The transducer operation, the signal producing electronics as well as the signal receiving and processing electronics, contribute to the wave shape of the signals as ultimately received and evaluated. It is, therefore, necessary to calibrate the transducers. For this, it has been necessary in the past to couple the transducer to a reference object or dummy preferably having dimensions, contour and acoustic properties equal to or at least closely matching the corresponding features of the test objects. The reference object is not only used for purposes of signal level calibration, gain adjustment, sensitivity and threshold adjustments, etc., but also for purposes of determining the requisite angles of incidence for the test beams, the skip distance in the case of testing pipes or plates, and the requisite actual distance needed for a specific task.

The use of such calibration objects was found to be a problem in some instances. Take, for example, the following situation. It appears that a best suited reference object is a test object known, e.g. to have no defects. It may be the first or one of the first objects made, or a portion of an object made in a first production run, being a part of a pilot series, etc. The thus chosen object is now provided with a definite "defect" to be used as a reference in the calibration procedure. It was found that this defect simulation is not sufficiently accurate nor are such simulated errors accurately reproducible if different reference objects are made. Another point is the delay incurred when the calibration object is taken from the production which must be halted until the calibration has been completed.

A test procedure has been suggested (U.S. Pat. No. 4,106,326, which eliminates the disadvantages outlined above by using a particular reference object or dummy in a separate calibration installation to ascertain operating parameters for the test electronics as well as the test heads, simulating true test conditions. A particular test standard or reference element (to be distinguished from the reference object or dummy) is then used in the calibration installation as adjusted to generate particular responses. That standard is then temporarily installed in the on-line test equipment and its electronics is then adjusted on the basis of the responses one obtains with the standard in comparison with the responses the same standard involved in the calibration electronics. This procedure operates quite satisfactorily, particularly because the calibration can be made ahead of production runs. A standard or reference element to be used for that purpose is disclosed in U.S. Patent application Ser. No. 878,240, filed Feb. 16, 1978. Utilization of this reference element was found to be suitable and reliable. Nevertheless, the reference element is used in conjunction with calibrating procedure that must precede test and production runs.

DESCRIPTION OF THE INVENTION

It is an object of the present invention to further simplify calibration procedure in ultrasonic test equipment.

It is a specific object of the present invention to approach calibration differently as compared with prior practice.

In accordance with the preferred embodiment of the present invention, it is suggested to incorporate a calibration device in each transducer of an ultrasonic test apparatus in that such a transducer is provided with a partial reflector in front of its transducing surface, but sufficiently far from the interface with the test object. This reflector provides an echo for each pulse launched which echo can be used for calibration. By way of example, the reflector may be a wire or a bore in a solid transmissive medium in front of the transducing surface. The major portion of transducing energy is always permitted to pass so that the "calibration echo" does not subtract any significant amount of test energy from the launched pulse. The calibration procedure is, therefore, greatly simplified and no longer separated from the test runs. Moreover, the calibration echo is always available and readily distinguishable from other echos on account of the transit time. The calibration, may, in fact, become a part of the test procedure itself so that updating and any readjustment can be made at any time during testing without interruption of the on-line operation or any portion thereof.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding to the detailed description of the drawings, FIG. 1 illustrates an ultrasonic transducer 1, having an active vibrating or externally stimulated vibrating element 2, respectively, for launching or receiving ultrasonic signals. This portion of the transducer is conventional; i.e. it is constructed to emit ultrasonic waves upon being electrically stimulated, while generating electrical signals when being acoustically stimulated. Also conventionally is the use of electronic circuitry in conjunction with that transducer including particularly circuitry which switches over from the transmitter mode to the receiver mode once an ultrasonic pulse has been launched.

The transducer is contained in a sleeve 3 for purposes of mounting. The front of the sleeve projects beyond the transducing surface 2'. Conceivably, the space adjacent to that surface 2' is filled with water during test operations. The front end of that sleeve may engage the test object, however, the interface may be somewhat further away still. The sleeve should have poor propagative properties as to acoustic waves, or at least may be provided with some attenuating means, so that ultrasonic waves are not launched via the sleeve 3. A relatively thin wire 4 is placed diametrically across the space in front of surface 2', and at a particular, well defined distance therefrom. The area covered by the wire 4 in front of surface 2' is small in relation to the area of that surface. Since the propagation path from the vibrating element to the wire has good propagative properties, there is little attenuation and a finite amount of acoustic energy is reflected back to the transducer. That amount will produce a definite response, i.e. it is sufficiently strong, being as far as the amplitude is concerned, of the order of flaw echos, which the transducer may receive when coupled to a test object. On the other hand, the partial reflection on wire 4 diminishes the launched energy to a very small extent only so that the test is not interferred with.

In operation, the head as depicted, i.e. including its calibration, reflector element 4, is installed in the test equipment which is now calibrated in situ. The response of the electronics, with head installed, to the echo from the wire is and remains an operating parameter. During test runs there will always be an echo from wire 4 so that the equipment can be recalibrated whenever needed.

The echo can actually be used in each test cycle as one of the measuring parameters. Since the wire 4 is also spaced from the interface between, on one hand, the transducer and the coupler fluid, and, on the other hand, the test object, the echo from wire 4 can readily be distinguished from any other echos on the basis of the transit time. The wire echo will occur at a rather precisely defined period of time following launching and positively before, e.g. a front wall echo on test objects' surface. The wire 4 must be spaced sufficiently far from surface 2' so that the transducer can readily be switched in time from the transmitter to the receiver mode. Also, the transducer as such should have recovered before the calibration echo arrives.

Since the calibration feature becomes a permanent part of the test head, there is an inherent compensation of any manufacturing tolerances. Also, any external interferences with the operation can readily be recognized by, e.g. a change in the amplitude of the calibration wire echo. Moreover, the initialization and set up procedure of the test equipment is shortened.

Figure 1:
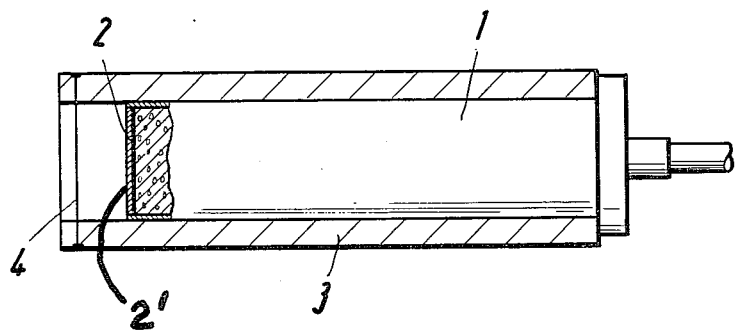
FIG. 1 is a cross-section through a test head supplemented in accordance with the preferred embodiment of the invention, showing a particular example.
Figure 2:
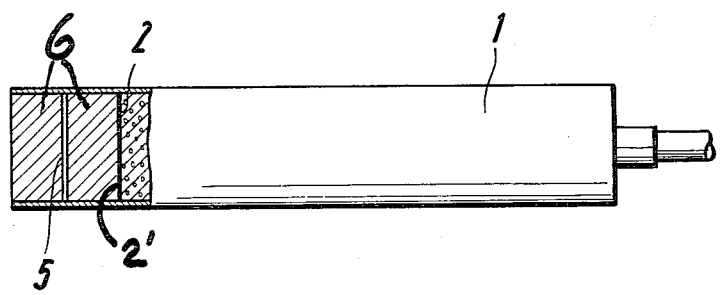
FIG. 2 is a similar cross-section showing a modification but still within the purview of the preferred embodiment.

FIG. 2 illustrates a variant in the construction to be used either when coupler fluid is not employed or if one does not wish to extend any coupler fluid directly to the active transducing surface 2'. The transducer jacket has been extended here in forward direction, though a sleeve, such as 3 of FIG. 1, could also be used. The front end of the transducer jacket is filled with a plastic material 6 of particular acoustic properties. The material should not attenuate the acoustic energy, exhibit little dispersion and should not tend to reverberate. One can use here Plexiglas, Polystyrol or others.

The material 6 is provided simply with a bore 5 extending in diametrical direction across the space in front of the transducing surface 2' and also at a well defined distance therefrom. The bore 5, in this case, acts as calibration and reference reflector just as wire 4 in FIG. 1. The advantages and features outlined above are also applicable here.

The invention is not limited to the embodiments described above but all changes and modifications thereof not constituting departures from the spirit and scope of the invention are intended to be included.

We claim:
1. Transducer head for ultrasonic testing of structural materials having a transducing surface, comprising:
   a means for defining an acoustic wave propagative path in front of the surface; and
   a calibration reflector disposed across the path in front of the said surface and at a distance therefrom for intercepting a central portion and reflecting a small portion of any ultrasonic energy launched by the transducer, but permitting the major portion of that energy to pass said reflector on both sides due to the extension of the reflector across the path of the energy.

2. Transducer head as in claim 1, said reflector being a wire.

3. Transducer head as in claim 1, there being an acoustic energy transmissive material in said path, said reflector being a bore in the material.

* * * * *